(12) United States Patent
Ackerman et al.

(10) Patent No.: US 6,821,256 B2
(45) Date of Patent: Nov. 23, 2004

(54) NON-ALTERNATING BEAT-TO-BEAT FLUCTUATIONS IN T WAVE MORPHOLOGY

(75) Inventors: Michael J. Ackerman, Rochester, MN (US); Jan Nemec, Praha (CZ); Win-Kuang Shen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 24 days.

(21) Appl. No.: 09/775,176

(22) Filed: Feb. 1, 2001

(65) Prior Publication Data

US 2002/0143265 A1 Oct. 3, 2002

(51) Int. Cl.[7] .............................................. A61B 5/0452
(52) U.S. Cl. ...................................................... 600/508
(58) Field of Search ................................ 600/300, 508, 600/509, 515, 517

(56) References Cited

U.S. PATENT DOCUMENTS

| | | | |
|---|---|---|---|
| 4,622,980 A | * | 11/1986 | Kunig .......................... 600/517 |
| 5,570,696 A | | 11/1996 | Arnold et al. |
| 5,673,702 A | | 10/1997 | Albrecht et al. |
| 5,713,367 A | | 2/1998 | Arnold et al. |
| 5,891,045 A | | 4/1999 | Albrecht et al. |
| 5,891,047 A | | 4/1999 | Lander et al. |
| 5,935,082 A | | 8/1999 | Albrecht et al. |
| 6,016,443 A | * | 1/2000 | Ekwall et al. .............. 600/519 |
| 6,047,206 A | | 4/2000 | Albrecht et al. |
| 6,285,898 B1 | * | 9/2001 | Ben-Haim ................... 600/374 |

OTHER PUBLICATIONS

Couderc et al., *PACE*, 1999, 22:1581–1592.
Chialvo & Jalife, *Nature*, 1987, 330(6150):749–752.
Chialvo et al., *Nature*, 1990, 343(6259):653–657.
Karagueuzian et al., *Circulation*, 1993, 87(5):1661–1672.

* cited by examiner

*Primary Examiner*—George R. Evanisko
(74) *Attorney, Agent, or Firm*—Fish & Richardson P.C., P.A.

(57) ABSTRACT

The invention features methods to detect T wave lability in an individual, and methods of using T wave lability to detect or monitor abnormal cardiac activities. An individual can be assessed for the risk of sudden death due to cardiovascular pathology using methods provided by the invention. The invention also features methods of obtaining a T wave lability index for an individual. The invention further features a computer-readable storage medium for calculating an individual's T wave lability index and an apparatus for obtaining same. In addition, the invention features an article of manufacture for chemically stressing an individual for the purpose of determining a T wave lability index.

11 Claims, 6 Drawing Sheets

NON-ALTERNATING BEAT-TO-BEAT FLUCTUATIONS IN T WAVE MORPHOLOGY

TECHNICAL FIELD

This invention relates to the physiology of the heart, and more particularly, to non-alternating beat-to-beat fluctuations in T wave morphology.

BACKGROUND

The human heart is a four-chambered, muscular pump that contracts rhythmically due to the presence of cardiac muscle tissue. The heart is contained behind the sternum and within the cavity between the lower halves of the lungs. The heart lies within a double-walled sac called the pericardium, whose lower margin is anchored to the diaphragm. Thus, the heart is separated from the rest of the thoracic cavity, enclosed in a sac that serves as a protection against mechanical injury. The heart is divided into two distinct halves by a muscular wall called the septum. The right half receives blood that contains deoxygenated hemoglobin, while the left side receives blood containing oxygenated hemoglobin. Each side of the heart is divided into two chambers. Those at the top of the heart are called the atria and below them are the ventricles. The openings between the atria and the ventricles are guarded by atrioventricular valves, which prevent blood from passing back into a chamber.

Blood from throughout the body enters the right atrium through the superior and inferior venae cavae. Blood then flows into the right ventricle, and is pumped into the pulmonary artery and into the lungs, where contaminants (e.g., carbon dioxide) are removed and the blood is oxygenated. The oxygenated blood then flows back into the heart (i.e., the left atrium) via the pulmonary veins, flows into the left ventricle, and from there, is pumped into the aorta, which, via other arteries and capillaries, distributes the oxygenated blood throughout the body.

SUMMARY

The invention describes novel non-alternating fluctuations in T wave morphology following chemical stress of an individual. These non-alternating fluctuations in T wave morphology are termed T wave lability. The invention provides for methods of detecting T wave lability in the cardiac electrical signals of an individual. The detection of T wave lability can be used in methods of the invention to detect or monitor abnormal cardiac activities in an individual, or to assess the risk of an individual for sudden death due to cardiovascular pathologies. The amount of T wave lability can be quantitated and used in methods provided by the invention to calculate a T wave lability index. The invention further provides a computer-readable storage medium for calculating a T wave lability index, as well as an apparatus for detecting T wave lability and for calculating a T wave lability index for an individual. The invention also provides an article of manufacture for chemically stressing an individual for the purpose of determining a T wave lability index.

In one aspect, the invention provides a method of detecting T wave lability in an individual. T wave lability is detected by obtaining signals representative of electrical activity of the heart of the individual and detecting any non-alternating beat-to-beat fluctuations in the morphology of the T wave. Such non-alternating beat-to-beat fluctuations in the T wave morphology are indicative of the individual having T wave lability.

In another aspect, the invention provides a method for detecting or monitoring abnormal cardiac activities in an individual, including obtaining signals representative of electrical activity of the heart and detecting the presence of non-alternating beat-to-beat fluctuations in T wave morphology. The presence of non-alternating beat-to-beat fluctuations in T wave morphology indicates abnormal cardiac activities in the individual.

In yet another aspect of the invention, there is provided a method of obtaining a T wave lability index, including obtaining signals representative of electrical activity of the heart of an individual, eliminating ectopic beats and the sinus beats preceding and following the ectopic beats, and calculating the maximal value of root-mean-square differences for isochronic points of the repolarization interval between pairs of consecutive beats. Generally, ectopic beats include a ventricular premature contraction or an atrial premature contraction. In certain embodiments, the signal can be filtered, baseline fluctuation can be removed, and/or the maximal value of root-mean-square differences can be normalized to the absolute magnitude of the signal-averaged QRS complex.

The invention also provides a method of identifying non-alternating beat-to-beat fluctuations in T wave morphology in cardiac electrical signals, and calculating a T wave lability index as a function of the non-alternating beat-to-beat fluctuations in T wave morphology.

In still yet another aspect of the invention, there is provided a method of assessing the risk of an individual for sudden death due to cardiovascular pathology. This method includes obtaining signals representative of electrical activity of the heart of the individual, detecting the presence of non-alternating beat-to-beat fluctuations in T wave morphology in the cardiac electrical signal, and determining a T wave lability index from the non-alternating beat-to-beat fluctuations in T wave morphology. A T wave lability index that is significantly different than a reference value indicates an increased risk of the individual for sudden death due to a cardiovascular disease. Individuals at risk for sudden death due to cardiovascular pathology may present with QT prolongation, QT variability, ectopy, TWA, OHCA, syncope, angina, late potentials, QT dispersion, wide complex tachycardia, unexplained seizures or unexplained near drownings. Representative examples of cardiovascular pathologies include long QT syndrome, hypertrophic cardiomyopathy, dilated cardiomyopathy, coronary artery disease, myocardial ischemia, idiopathic ventricular fibrillation and Brugada syndrome.

Generally, a chemical stressor is administered to an individual with regard to practicing the above-described methods. Representative chemical stressors include catecholamine compounds, such as dobutamine, epinephrine, phenylephrine and atropine. Typically, the amount of the chemical stressor is selected to achieve a heart rate within a desired range, for example, greater than 100 beats per minute (bpm).

In addition, the invention further provides a computer-readable storage medium having instructions stored thereon for causing a programmable processor to identify non-alternating beat-to-beat fluctuations in T wave morphology in signals representative of electrical activity of the heart of an individual and determine a T wave lability index as a function of the non-alternating beat-to-beat fluctuations in T wave morphology. As used herein, ectopic beats include ventricular premature contractions and atrial premature contractions. Typically, the processor determines a T wave lability index as a function of the non-alternating beat-to-beat fluctuations in T wave morphology by eliminating ectopic beats and the sinus beats preceding and following the ectopic beats and calculating the maximal value of root-mean-square differences for isochronic points of the repolarization interval between pairs of consecutive beats. The processor can also perform functions such as filtering the signal, removing baseline fluctuation and normalizing the maximal value of the root-mean-square differences to the absolute magnitude of the signal-averaged QRS complex.

The invention also provides an apparatus for determining a T wave lability index for an individual. The apparatus can include one or more transducers for obtaining signals representative of electrical activity of the heart of the individual and a processor for analyzing the electrical signals and determining the T wave lability index. By way of example, the transducers can be electrodes. In one embodiment, the apparatus generates a visual representation of the electrical signals. In another embodiment, the apparatus generates a signal indicative of the presence of ectopic beats. Generally, obtaining and analyzing the signals occurs concurrently.

The signals representative of electrical activity of a heart are oftentimes generated into an electrocardiogram. Electrical signals obtained from a precordial lead V4 are exemplified herein. In addition, the heart rate of the individual is usually monitored during a procedure to determine T wave lability and a T wave lability index.

In another aspect of the invention, there is provided an article of manufacture for chemically stressing an individual for the purpose of determining a T wave lability index for the individual. The article of manufacture (i.e., a kit) can include a vial comprising an appropriate dose of a catecholamine compound, at least one additional vial comprising a different dose of the same or a different catecholamine compound, and a label or package insert that indicates that the contents can be used in a procedure to determine a T wave lability index. Oftentimes, the doses are different concentrations of catecholamine compounds and each of the vials are preferably labeled with the respective dose.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Experiments described herein reveal that catecholamine provocation with phenylephrine or dobutamine can induce non-alternating beat-to-beat variability of the repolarization segment in patients carrying mutations that result in the three most common long QT syndromes (LQTS), but in none of the control subjects. This variability is of sufficient magnitude to permit assessment by calculating the root-mean-square differences in amplitude between pairs of non-ectopic subsequent beats. Furthermore, results indicate a highly significant association between the novel catecholamine-provoked non-alternating beat-to-beat fluctuations in T wave morphology, termed T wave lability, and clinical risk. Therefore, determination of a T wave lability index (TWLI) by quantitating T wave lability can permit identification of asymptomatic individuals at risk for cardiac abnormalities or cardiovascular pathologies.

The invention features methods of detecting T wave lability in an individual, and methods for calculating a T wave lability index. The invention further provides methods of using T wave lability to detect or monitor an individual for abnormal cardiac activities and methods of using the T wave lability index to assess the risk of an individual for sudden death due to a cardiovascular pathology. Also provided by the invention are computer readable media that can direct a processor to analyze T wave lability and calculate a T wave lability index. An apparatus for obtaining electrical cardiac signals, determining T wave lability and calculating a T wave lability index is further provided by the invention. Articles of manufacture, including one or more catecholamine compounds, are provided by the invention for the purpose of chemically stressing an individual to determine a T wave lability index.

T Wave Lability

The observation of macrovoltage non-alternating beat-to-beat flucuations in T wave morphology (herein termed "T wave lability") is a novel phenomenon. The invention features methods of detecting T wave lability in an individual. T wave lability is detected by administering one or more chemical stressors to an individual and obtaining electrical signals that are representative of cardiac activity. The detection of non-alternating beat-to-beat fluctuations in T wave morphology in the cardiac signals indicates the presence of T wave lability in the individual.

The phenomenon of catecholamine-provoked T wave lability is clearly different from T wave alternans (TWA) and, in fact, there was no periodicity observed in the fluctuations in T wave morphology in the subjects described herein. Interestingly, T wave lability would appear as broadband noise in the power spectrum of a TWA analysis, thereby masking potential $\mu$V-TWA by decreasing the signal-to-noise ratio. Further, while TWA is a heart-rate induced phenomenon (i.e., detection of TWA usually requires a physiological stress such as exercise), T wave lability is observed following chemical provocation with, for example, $\beta$-sympathetic agents (e.g., dobutamine, epinephrine), parasympathetic blocking agents (e.g., atropine), or vasoconstrictors (e.g., epinephrine, phenylephrine).

Chemical stressors used in methods of the invention can be catecholamine compounds, such as dobutamine, epinephrine, phenylephrine or atropine. The amount of chemical stressor to be administered to an individual is usually based upon the individual's weight, and can be administered in a dose that achieves a heart rate within a desired range. Oftentimes, but not necessarily, this range is greater than 100 beats per minute (bpm) but typically does not exceed 140 bpm. The heart rate of an individual is generally monitored when undergoing chemical stress to detect T wave lability.

For a visual representation, the electrical signals can be generated into an electrocardiogram. As used herein, an electrocardiogram (ECG) is a body-surface recording of the electrical activity of the heart as a continuous function of time taken by an electrocardiograph machine. A standard ECG usually includes the following 12 leads: I, II, III, aVR, aVL, aVF, V1, V2, V3, V4, V5 and V6. Alternatively, an ECG can be a bipolar, a multi-polar or a Laplacian ECG. The number and placement of electrodes on an individual is known to those of skill in the art to obtain the desired electrical signals. Electrical signal obtained from the precordial lead V4 is exemplified herein, but the signal may be obtained from other or multiple leads. Using the methods described herein, the spatial and temporal heterogeneity in T wave lability using various leads can be readily determined for a number of other cardiovascular pathologies.

An individual who is a candidate for a chemical stress procedure to assess T wave lability may present with symptoms such as syncope, angina, unexplained seizures, unexplained near drowning, or OHCA, or may present with electrocardiographic findings of ectopy, QT prolongation, QT variability, TWA, late potentials, QT dispersion or wide complex tachycardia. Alternatively, a candidate individual can be diagnosed with a genetic predisposition for a cardiovascular pathology or may have undergone a revascularization procedure such as balloon angioplasty. The method also can be used preventatively to screen individuals, for example, during a routine physical or after negative indications in a cardiac stress test. Cardiac stress testing is performed more than 8 million times a year in the United States (U.S.) alone, and is widely used as the initial assessment of whether coronary artery disease is altering the function of the heart. The ability to examine T wave lability as described above allows for a non-invasive method to detect or monitor abnormal cardiac electrical activities in an individual.

T Wave Lability Index

The amount of T wave lability, i. e., the degree of non-alternating beat-to-beat fluctuations in T wave morphology, can be quantitated to obtain a T wave lability index. The method of obtaining a T wave lability index includes obtaining electrical cardiac signals from an individual, eliminating ectopic beats and the sinus beats immediately preceding and following the ectopic beats and calculating the maximal value of root-mean-square differences for isochronic points of the repolarization interval between pairs of consecutive sinus beats. Ectopic beats can include, for example, a ventricular premature contraction or an atrial premature contraction. The electrical signals representative of cardiac activity can be filtered and/or baseline fluctuation can be removed from the signal prior to calculating the maximal value of root-mean-square differences. The maximal value of root-mean-square differences also can be normalized to the absolute magnitude of the signal-averaged QRS complex. Normalization of the data results in ECG signals that are comparable to each other either between different locations on the body surface or between different individuals. Physiologically, the QRS complex of an ECG beat corresponds electrically to contraction of the ventricles of the heart, while the T wave component corresponds to electrical recovery, or repolarization, of the ventricles.

Calculating a T wave lability index as described above allows for a method of assessing the risk of an individual for sudden death due to cardiovascular pathology. A T wave lability index that is significantly different than a reference value indicates an increased risk for sudden death due to a cardiovascular pathology. Therefore, calculating a T wave lability index can be used to risk stratify individuals for sudden death. A variety of methods are currently used to risk stratify individuals with cardiac abnormalities, including measurement of the ejection fraction of the heart, measurement of the signal average ECG, measurement of heart rate variability, and measurement of ambient ventricular ectopic activity on a 24 hr ECG. These methods generally are not sufficiently predictive of risk to justify most cardiac treatment regimens.

The reference value is an average T wave lability index determined for multiple control individuals. Control individuals used to generate a reference value are preferably normal healthy individuals with no evidence of underlying cardiac disease. Control individuals can be, but do not necessarily need to be, age-matched and/or gender-matched with the individual(s) being evaluated for risk of sudden death. For determining a reference value, the number of control individuals should be at least 3, for example, 5, 10, 20, 50 or 100 or more control individuals. "Significant difference" refers to a statistically significant difference ($p \leq 0.05$, for example, $p \leq 0.025$ or $p \leq 0.01$) between the T wave lability index of an individual being evaluated for risk of sudden death and a reference value and can be determined using an appropriate measure of statistical significance (e.g., two-sided Wilcoxon rank sum test).

Following risk assessment, an individual can be treated accordingly. Effective means are available to treat individuals with electrical instabilities of the heart. For example, implantable cardioverter-defibrillators (ICD's) are effective in preventing sudden cardiac death. This device can terminate ventricular tachycardia and fibrillation by delivering an electrical shock to the heart. In addition, anti-arrhythmic drugs are available which modify the electrical properties of the heart. Use of these drugs under appropriate conditions can render the heart more electrically stable.

Catecholamine-provoked T wave lability represents a new type of repolarization instability distinct from T wave alternans and from previously reported abnormalities of QT duration variability. T wave lability was inducible by catecholamine stimulation in LQTS patients of diverse genotypes. The strong association between an elevated T wave lability index and sustained catecholamine-induced VT, OHCA history, or syncope plus sudden death in the family, indicates that TWLI may afford a novel marker for clinical risk stratification in congenital LQTS and other cardiovascular pathologies, such as those in which temporal abnormalities of ventricular repolarization have been detected.

LQTS Cardiovascular Pathologies

LQTS, a primary channelopathy of the heart, represents a human molecular model for the study of ventricular arrhythmogenesis. Mutations in three genes encoding ion channel alpha-subunits [KVLQT1 (LQT1), HERG (LQT2), SCN5A (LQT3)] and in two genes encoding ion channel modifying beta-subunits [hKCNE1 or minK (LQT5) and hKCNE2 or MiRP1 (LQT6)] provide the molecular/genetic substrate for approximately 50% of families with LQTS. In general, these ion channel perturbations result in an imbalance between depolarizing and repolarizing currents during phases 2 and 3 of the myocardial action potential that manifests on the surface ECG as QT prolongation. Clinically, the LQTS substrate may reveal its presence by syncope, seizures, or sudden death following degeneration of the previously stable, albeit sluggish, repolarization properties to a potentially lethal polymorphic ventricular tachyarrhythmia of torsades de pointes.

Unfortunately, no single risk factor has emerged indicating whether a person is likely to remain asymptomatic, as is seen in 40% of LQTS, or whether or not a person will present with sudden death. Previously reported negative prognostic factors include a history of aborted cardiac arrest, family history of at least one sudden unexplained death, macroscopic TWA, notched T waves and marked QT prolongation (QTc>550 ms). The predictive values of these risk factors, however, remain uncertain. Moreover, most LQTS-triggered events occur in the setting of sympathetic stimulation.

Treatment with β-blockers remains the cornerstone therapy for all long QT syndromes. Treatment with β-blockers is effective in many congenital LQTS patients. Some patients die suddenly, however, despite β-blockade or a combination of β-blockade and permanent pacemaker implantation. If these at-risk individuals could be identified prospectively, then primary prevention utilizing ICD would be life-saving. Recent evidence also is beginning to cast some doubt on the role of β-blockers in the treatment of patients with a sodium channelopathy (LQT3), as there was no apparent protective effect of β-blockers on reducing cardiac events in 28 patients studied with LQT3.

In the study described herein, only 1 of the 6 subjects deemed to be high clinical risk by virtue of either experiencing out-of-hospital cardiac arrest or having a history of syncope and at least one sudden death in the family displayed ominous QT interval prolongation on resting ECG. None of the subjects had macroscopic TWA or notched T waves at rest. Since nearly 30% of genetically affected subjects can have normal QT duration on 12-lead ECG (QTc<460 ms), there is a substantial overlap between the QTc of affected and unaffected subjects. On the other hand, the T wave lability described herein and the T wave lability index calculated therefrom is significantly different ($p<0.003$) between those individuals deemed at clinical risk and control individuals.

Other Cardiovascular Pathologies

Disturbances of electrical conduction processes in the heart are a major cause of morbidity and mortality. Sudden cardiac death, resulting from disturbances of electrical conduction in the heart, causes about 400,000 fatalities per year in the U.S. alone.

As used herein, fibrillation is when the heart beats so quickly and chaotically that it cannot effectively pump blood. Atrial fibrillation is a frequent cause of arrhythmia and often stems from hypertensive heart disease or pericarditis. Atrial fibrillations can usually be treated with drug therapy. Ventricular fibrillation can lead to cardiac arrest or death of heart muscle (myocardial infarction). Cardiac arrest, or a heart attack, is when the heart stops pumping blood through the body. This can occur because the ventricles are beating too erratically to effectively pump blood or because the heart stops beating at all. Heart attack victims quickly lose consciousness, their pulse disappears and they stop breathing. Emergency measures include cardiopulmonary resuscitation (CPR) and defibrillation. Myocardial infarction generally refers to the death and scarring of a section of heart muscle caused by a progressive loss of blood flow from a coronary artery. Myocardial infarctions often occur in the left ventricle and cause sharp pain in the chest, which can subsequently spread to the arms and throat. Each year in the U.S. alone, more than a million people experience a myocardial infarction.

Congestive heart failure (CHF) generally refers to global failing of the heart muscle and is characterized by low cardiac output, sodium and water retention, peripheral vasoconstriction and activation of the renin-angiotensin-aldosterone axis. As the heart muscle ceases to work, fluid accumulates in the lungs and body. Among the possible consequences of CHF are an inability to breathe, liver failure, hypertension, myocardial infarction and death. CHF is treated with diuretics or, in severe cases, a heart transplant.

Cardiomyopathy is any chronic disorder affecting the heart muscle. Possible conditions caused by cardiomyopathy include heart failure, arrhythmias and embolisms. Hypertrophic cardiomyopathy is characterized by an unexplained increase in the left ventricular wall thickness with or without obstruction. Dilated cardiomyopathy is characterized by progressive enlargement of the cardiac chambers.

Coronary artery disease generally refers to a lack of oxygen to the heart and the related problems that occur. Myocardial ischemia is the most common form of heart disease and typically refers to lack of oxygen to the heart due to narrowing of the arteries and hence, reduced myocardial blood flow. Idiopathic ventricular fibrillation refers to the occurrence of ventricular fibrillation in the absence of any structural heart disease or any relevant finding for the observed ventricular fibrillation. Brugada syndrome refers to a specific kind of ventricular fibrillation having a distinct ECG pattern generally consisting of right bundle branch block with ST segment elevation in the right precordial leads (V1, V2 and V3), a normal QT interval, and the absence of any structural heart disease.

Sinus beats or sinus rhythms generally refer to electrical complexes comprised of a P wave, a QRS complex, and a T wave, with one P wave preceding each QRST complex. As used herein, an ectopic beat refers to a premature heartbeat due to a contraction impulse from an abnormal source, and can include ventricular or atrial premature contractions. As used herein, tachycardia refers to an increase of the heart rate above the normal level. Ventricular tachycardia (VT) refers to a rapid heart rate stemming from ventricular excitation without control from the sinus or AV nodes. Among the possible causes of tachycardia are arrhythmias, illness, exercise, stress or excitement. As used herein, bradycardia refers to a slow heart rate. Sinus bradycardia refers to an abnormally slow sinus rhythm. Causes of bradycardia can include, for example, sinus node dysfunction, hypothyroidism, anorexia, or certain medications (e.g., αβ-blockers or $Ca^{2+}$-channel blockers).

Arrhythmogenesis, QT Prolongation and T Wave Lability

The current understanding of the relationship between arrhythmogenesis and QT prolongation is incomplete. On the cellular level, prolonged repolarization can result in early after depolarizations (EADs). In the setting of increased dispersion of refractoriness, this triggered activity could lead to phase 2 re-entry. Animal experiments using a myocardial wedge preparation show that LQTS-like conditions accentuate the normal differences in duration of repolarization between epicardial and midmyocardial cells. Limited animal experiments in a canine heart preparation under conditions simulating LQT3 implicate both triggered activity and functional reentry in VT genesis. Alternating duration of repolarization elicited by cycle length shortening occurred initially in the midmyocardial cells and was accompanied by increased transmural dispersion of refractoriness and, in some cases, polymorphic VT. These results suggest that an increase in dispersion of refractoriness is causally associated with VT onset in subjects exhibiting QT prolongation. The observations herein of profound beat-to-beat T wave lability apparent during catecholamine-provocation in an in vivo human model of LQT3 are consistent with these mechanistic insights.

Although the present invention is not bound to or limited by a particular mechanism of action, the following physiological mechanisms are possible. The repolarization lability could be caused by EADs originating in relatively small populations of myocardial cells. If the muscle mass involved in the genesis of an EAD were sufficiently small, current-load mismatch could prevent the localized EAD from depolarizing the rest of the ventricles and generating a QRS complex. However, the EADs might still electronically affect the shape of the T wave. EADs originating from different regions of the ventricle and absence of EADs in some beats could account for the beat-to-beat repolarization lability. Alternatively, the T wave lability could be caused by different APD/DI relationships in different segments of the ventricle and by electrotonic interactions between these segments. In the canine LQTS model, the prolongation of repolarization was significantly more pronounced in the lateral than in the septal area of the left ventricle. Both spatial heterogeneity in repolarization (QT dispersion) and transmural heterogeneity of repolarization across the ventricular wall occurred. Temporal repolarization patterns in electrically coupled ventricular segments with different APD/DI relationships, however, are much more complex than in an isolated cell and, therefore, could account for the non-alternating repolarization lability.

Of the 10 subjects with profound beat-to beat T wave lability examined herein (TWLI $\geq 0.095$), the isochronic point manifesting the maximum TWLI occurred after the peak of the T wave in 9 subjects. This result suggests heterogeneity of repolarization within localized M cells. Irrespective of whether the T wave lability is caused by multifocal EADs or by high and changing degrees of repolarization dispersion, both would increase the propensity for ventricular arrhythmias and cardiovascular pathologies.

Computer-readable Medium and an Apparatus for Determining TWLI

The invention further features a computer-readable storage medium configured with instructions for causing a programmable processor to identify non-alternating beat-to-beat fluctuations in T wave morphology in an individual's electrical cardiac signals and to calculate a T wave lability index as a function of the individual's T wave lability.

Figure 6:
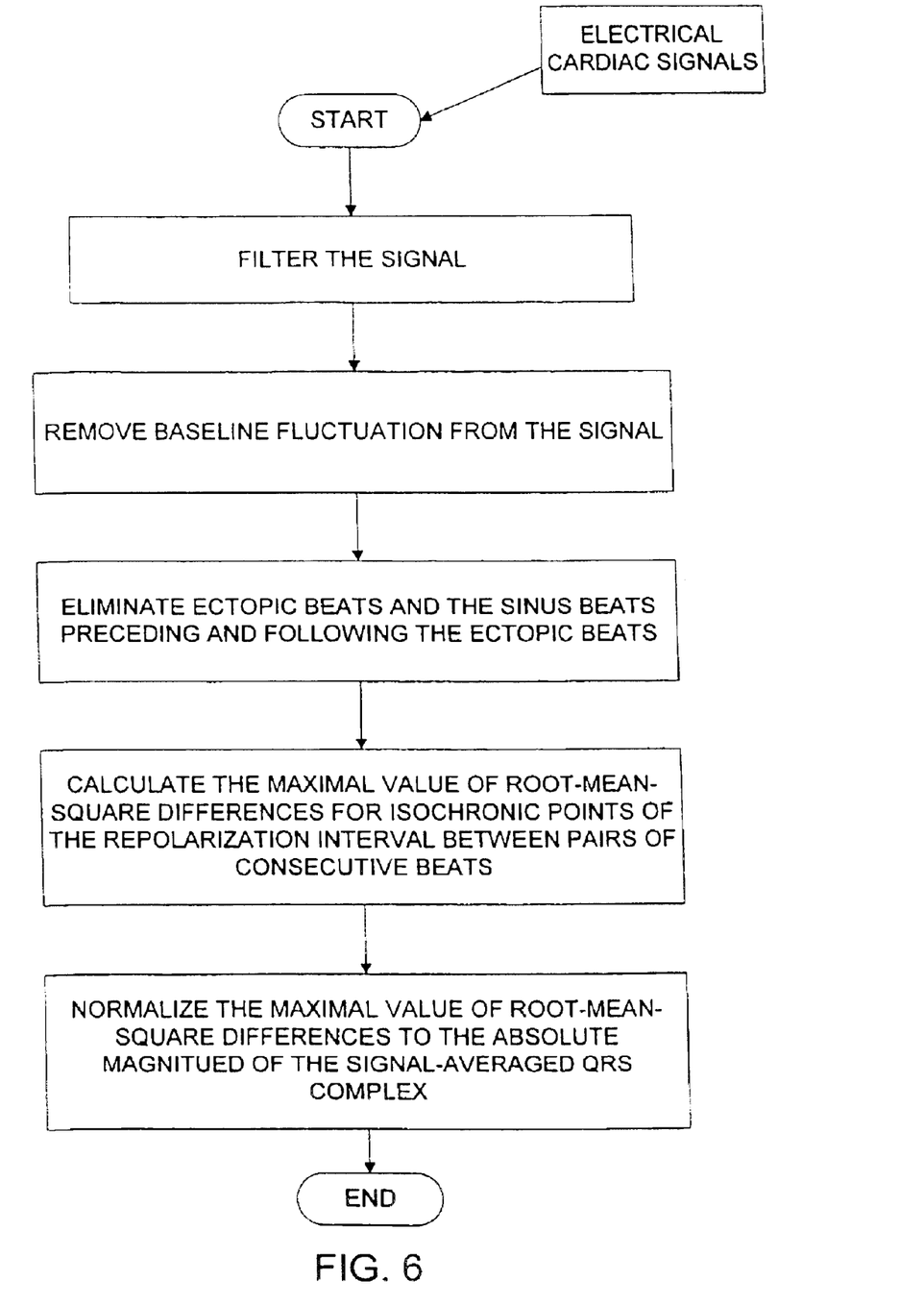
FIG. 6 shows an example of instructions for a processor to determine a T wave lability index.

The T wave lability index as a function of the non-alternating beat-to-beat fluctuations in T wave morphology is calculated as described above; that is, by eliminating the ectopic beats and the sinus beats immediately preceding and following the ectopic beats and calculating the maximal value of root-mean-square differences for isochronic points of the repolarization interval between pairs of consecutive beats. The processor also can be designed to perform functions such as removing baseline noise from the electrical signal or normalizing the maximal value of root-mean-square differences to the absolute magnitude of the signal-averaged QRS complex before providing a TWLI. FIG. 6 exemplifies one mode of operation by a processor for determining a T wave lability index.

Instructions carried on a computer-readable storage medium (e.g., for identifying T wave lability and calculating a TWLI) can be implemented in a high level procedural or object oriented programming language to communicate with a computer system. Alternatively, such instructions can be implemented in assembly or machine language. The language further can be compiled or interpreted language.

The electrical cardiac signals can be obtained using an apparatus (e.g., an electrocardiograph) and a TWLI can be generated using a separate processor (e.g., a computer). Alternatively, a single apparatus having a programmable processor can both obtain the electrical cardiac signals and process the signals to generate a TWLI. In addition, the processing step can be performed simultaneously with the step of collecting the electrical cardiac signals (e.g., "real-time"), thereby allowing the operator to monitor an individual's TWLI during chemical stress.

Another feature of the invention, therefore, is an apparatus for determining a T wave lability index for an individual. An apparatus for determining T wave lability index can include one or more transducers for obtaining electrical cardiac signals from the individual and a processor for analyzing the electrical cardiac signals and determining the T wave lability index. By way of example, the transducers can be standard electrodes (e.g., single terminal electrodes). Alternatively, specialized multi-segment or noise-reduction electrodes can be used to eliminate or reduce noise, interference, distortion, or artifacts. The apparatus further can generate a visual or graphical display of the electrical signals, such as a map (e.g., an isometric, contour, gray scale, color, polar image, isopotential or isochronous map) or a mechanical or digitized representation. The apparatus also can generate an indication of ectopic beats (e.g., audio or visual). The apparatus can further include a display that can be annotated to indicate the transition to a different catecholamine compound or different dose of a catecholamine compound administered to an individual. Such an apparatus also can be portable.

Articles of Manufacture

A vial containing an appropriate dose of a catecholamine compound and at least one additional vial containing an appropriate dose of the same or a different catecholamine compound can be combined with packaging material and sold as a kit for the purpose of chemically stressing an individual to determine a T wave lability index. Components and methods for producing articles of manufactures are well known in the art. Preferably, the doses are different concentrations of catecholamine compounds. In addition, it is common practice that the vials are labeled with the particular dose and compound. Instructions describing how an individual is to be chemically stressed for purposes of obtaining a T wave lability index and the particular doses to be administered may be included in such kits. Different kits may be manufactured with doses of catecholamine compounds appropriate to chemically stress an adolescent or young adult subject, an adult female subject or an adult male subject (based upon an average weight). Instructions can further include a table or chart for adjusting particular doses of a catecholamine compound for a subject that deviates from average.

The invention will be further described in the following examples, which do not limit the scope of the invention described in the claims.

EXAMPLE 1

Subject Population 23 subjects with genotyped congenital LQTS and 16 control subjects were studied. Two of the control subjects were unaffected members of the participating LQTS kindreds. In the LQTS cohort, three subjects had suffered confirmed out-of-hospital cardiac arrest (OHCA) of which two had been implanted previously with ICDs. Three additional LQTS subjects were deemed high clinical risk on the basis of a personal history of syncope and a family history of at least one sudden unexplained death. The control subjects were free of known cardiovascular disease except for mild hypertension in one subject. The demographic details are provided in Table 1.

TABLE 1

Demographic and Genetic Characteristics of the LQTS and Control Groups

|  | LQTS (n = 23) | Control (n = 16) |
|---|---|---|
| age (yr) | 26.3 ± 11.7 | 27.3 ± 12.5 |
| gender (M/F) | 8/15 | 6/10 |
| medications |  |  |
| β-blocker | 3 | 0 |
| diuretic | 0 | 1 |
| ACE-I | 0 | 1 |
| antidepressants | 2 | 3 |
| BCP/estrogen | 1 | 4 |
| mutations | # subjects (families) |  |
| LQT1 (KVLQT1) | 13 (8) | NA |
| F339del | 4 |  |
| T322A | 2 |  |
| stop @ 282 | 2 |  |
| V133I | 1 |  |
| R243C | 1 |  |
| Y315C | 1 |  |
| R555C | 1 |  |
| AAP71-73del | 1 |  |
| LQT2 (HERG) | 7 (4) | NA |
| 3080delG | 3 |  |
| 520insC | 2 |  |
| N633S | 1 |  |
| R582C | 1 |  |
| LQT3 (SCN5A) | 3 (1) | NA |
| E1784K | 3 |  |

NA, not applicable

EXAMPLE 2

Genetic Analysis

Genotyping of LQTS subjects was approved by the Mayo Foundation Institutional Review Board. Genomic DNA was extracted from peripheral blood lymphocytes using the Purgene DNA extraction kit from Gentra, Inc. (Minneapolis, Minn.). Using the full-length genomic DNA sequence and previously published intron/exon-based primers for KVLQT1, HERG, and SCN5A (Splawski et al. *Genomics*, 51:86–97, 1998 Wang et al. *Genomics*, 34:9–16, 1996), the 3 LQTS genes were systematically surveyed for LQTS disease-causing mutations. The mutation detection method involved exon-specific amplification by polymerase chain reaction and direct sequence analyses using manual ThermoSequenase sequencing (Amersham Life Science, Cleveland, OH) with $^{33}$P-labeled dideoxynucleotide triphosphates or automated fluorescent-based sequencing with the ABI 377 sequencer.

Specific LQTS mutations detected herein are designated in accordance with previously published recommendations for standard mutation nomenclature. Deletions are designated by "delNN" after the nucleotide number such that 1177–1179delAAG denotes the deletion of 3 nucleotides (AAG) from positions 1177 through 1179. Single basepair (bp) substitutions are denoted by the nucleotide number at which the substitution occurs. The first nucleotide following the number indicates the original nucleotide and the second nucleotide indicates the substitution. 967G>A denotes that at nucleotide 967 of a reference sequence, G is replaced by A.

At the level of the protein, the single letter amino acid code is utilized. To indicate an amino acid mis sense mutation and to distinguish amino acid nomenclature from that used for nucleotides, the format G269S is used. Here, the "wild type" amino acid (G=glycine) is given prior to the codon number (269), and the mutant amino acid (S=serine) is provided after the position. Deletions of amino acids are designated as AAP71–73del, for example. This indicates that residues 71 through 73 encoding alanine (A), alanine (A), and proline (P) are deleted. Finally, donor splice mutations are indicated by SP (splice) followed by the last amino acid and codon number at the end of the exon just prior to the splice site.

Table 1 shows the mutations detected and the number of individuals possessing each mutation for the LQT1, LQT2, and LQT3 subjects examined. Eight different LQT1 (KVLQT1) mutations (V133I, 735–739delGCGCT (stop@282), T322A, F339del, AAP71–73del, R243C, Y315C and R555C), four different LQT2 (HERG) mutations (R582C, N633S, 520insC (stop@331) and 3080delG (stop@1056)), and one LQT3 (SCN5A) mutation (E1784K) were determined for the 13 subjects with LQT1, 7 subjects with LQT2, and 3 subjects with LQT3, respectively.

EXAMPLE 3

Catecholamine-provocation Protocol and Dobutamine Stress Electrocardiogram

The study protocol was approved by the Institutional Review Board of the Mayo Foundation. All subjects provided written informed consent. A negative pregnancy test was required for female subjects of childbearing potential. During each stage of the study, a 12-lead ECG was recorded (for approximately 300 beats) while the subject was in a supine position during metronomic breathing. The data were stored on a magneto-optical disk using an EP Lab recording system (Quinton Electrophysiology Corp., Bothell, Wash.). The blood pressure of each subject was monitored non-invasively throughout the test using a Finapress device. Electrocardiographic recordings were performed at baseline, after administration of phenylephrine (2 µg/kg IV), and during increasing rates of intravenous dobutamine infusion (5, 10, 20, 30 µg/kg/min). The interval between phenylephrine administration and initiation of the dobutamine infusion was 10 min. After increasing the dose of dobutamine, 5 min were allowed to achieve a new steady state before recording. If a heart rate≧140 bpm was not reached by the end of the dobutamine infusion, atropine was given (0.5–1.0 mg IV). Finally, recovery phase electrocardiograms were obtained and the degree of T wave lability was determined at 10 and 20 min post-recovery (e.g., after stopping dobutamine). In addition to heart rate≧140 bpm, criteria for protocol termination included presence of macrovoltage TWA, frequent ventricular premature complexes (VPCs) (>10/min), complex ventricular ectopy or VT, severe nausea, vasovagal symptoms, chest discomfort, or blood pressure exceeding 220/140. Mild nausea during dobutamine infusion was treated with ondansetron.

EXAMPLE 4

Catecholamine-provoked T Wave Lability Analysis and Calculation of T Wave Lability Index (TWLI)

T wave lability was quantified by deriving a formula that calculates a T wave lability index (TWLI) using the following analytical methods. The recordings from the V4 lead were first low-pass filtered at a cutoff frequency of 20 Hz with a digital 3-pole Butterworth filter. Baseline fluctuation was reduced by interpolating fiducial points (preceding each R wave peak by 50 ms) with a cubic spline. For each isochronic point of the repolarization interval (from 110 ms after the R wave peak to the peak of the next R wave less 200 ms), the root-mean-square difference between corresponding signal values of all pairs of consecutive beats was calculated for each stage. Pairs of QRST complexes that included a VPC, an atrial premature complex (APC) or a sinus beat preceding or following a VPC or an APC were excluded. The maximal value of the root-mean square differences (corresponding to the specific isochronic point of maximal lability during the ST-T segment of repolarization) was determined for each recording. In order to account for differences of body habitus, maximal value of the root-mean square differences was normalized to the absolute magnitude (maximal minus minimal voltage) of the signal-averaged QRS complex. This value (maximal lability of ST-T segment normalized for QRS amplitude) is referred to as the T wave lability index (TWLI). The highest TWLI value and the study stage at which it occurred (at rest or during phenylephrine- or dobutamine-provocation) were recorded for each subject.

EXAMPLE 5

Statistical Analysis

All continuous variables were expressed as mean±standard deviation. Two-sided Wilcoxon rank sum test was used to compare maximal TWLI values between the LQTS patients and control subjects. Fischer's exact test was used to test independence of high TWLI with the clinical assignment of high risk. The Spearman rank correlation coefficient was used to evaluate the correlation between TWLI and baseline QTc. All calculated p values were two-sided and p<0.05 were statistically significant.

EXAMPLE 6

Microvoltage T Wave Alternans ($\mu$V-TWA) and LQTS

All 16 control subjects completed the entire protocol, with each individual achieving the target heart rate of 140 bpm. Atropine was necessary to achieve the target heart rate in 10 control subjects. In contrast, only 11 out of 23 LQTS patients reached the target heart rate. The study was terminated at lower heart rates in 12 LQTS patients because of ectopy (6), nausea (3), chest pain (2) and macrovoltage TWA (1) during dobutamine infusion.

A 14-year-old white male (previously genotyped for F339del-KVLQT1 with a prior history of OHCA) developed rapid polymorphic VT during dobutamine infusion (20 $\mu$g/kg/min). This led to loss of consciousness within about 10 sec and required external defibrillation that promptly restored sinus rhythm. Dobutamine infusion was terminated and metoprolol was administered intravenously. There were no other serious adverse events. Some degree of nausea occurred in 6 control subjects and 11 LQTS patients.

EXAMPLE 7

Catecholamine-provoked Torsades De Pointes

In the 14-year-old male with LQT1 who developed VT, examination of the ECG data preceding the malignant tachyarrhythmia revealed beat-to-beat variability of the T wave morphology involving the sinus beats (FIG. 1). Waveform A shows that sinus rhythm was present at baseline and the T wave morphology was uniform. Waveform B shows that during infusion of dobutamine at 10 $\mu$g/kg/min, pronounced T wave notching developed accompanied by dramatic non-alternating beat-to-beat fluctuations in the T wave morphology (T wave lability; arrows). No ectopic beats were present. Waveform C shows that during dobutamine infusion at 20 $\mu$g/kg/min, frequent polymorphic ventricular ectopy appeared. Ventricular tachycardia (VT) was initiated by a short-long-short sequence. There was a marked difference between the T wave morphology of the first (i.e., short) and second (i.e., long) complex of the VT (arrows). Both were sinus beats. Waveform D shows that the rate of the polymorphic VT accelerated. Loss of consciousness occurred within approximately 10 sec. Waveform E shows that sinus rhythm was restored by external defibrillation. Dobutamine infusion was discontinued and 5 mg of metoprolol was administered intravenously. The T wave morphology was completely uniform 10 min after defibrillation.

The beat-to-beat T wave lability in this individual was aperiodic. It did not follow an alternating pattern and did not appear to be associated with changes in QT duration. A computer program was written in Turbo Pascal v 7.0 (Borland) that calculates a T wave lability index (TWLI), and a TWLI was determined in all 39 participants.

EXAMPLE 8

T Wave Lability Index (TWLI)

The subject with the catecholamine-triggered VT exhibited marked T wave lability in the stage preceding the sentinel event (TWLI=0.148 on 10 $\mu$g/kg/min of dobutamine), but not at baseline (TWLI=0.048) or after defibrillation, termination of dobutamine infusion and administration of metoprolol (TWLI=0.026, FIG. 2). Four consecutive non-ectopic QRST complexes from the V4 lead were overlayed. FIG. 2A shows that at rest, the T wave morphology was nearly uniform. FIGS. 2B and 2C are two different sets of 4 consecutive QRST complexes during dobutamine infusion at 10 $\mu$g/kg/min, and show that there was non-alternating beat-to-beat fluctuations in T wave morphology, particularly in the second component of the T wave. FIG. 2D shows that 10 min after defibrillation, the T waves were essentially superimposable.

Figure 1A:
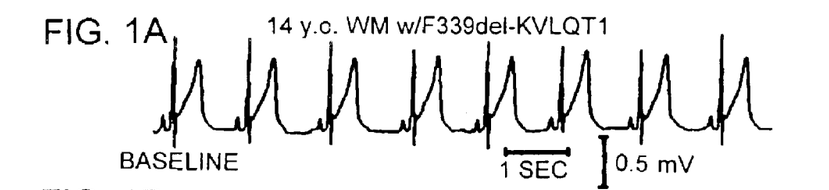
FIG. 1 shows dobutamine-triggered torsades de pointes in a 14-year-old male subject with LQT1 (F339-KVLQT1). Relevant ECG strips from the V4 lead are shown.
Figure 1B:
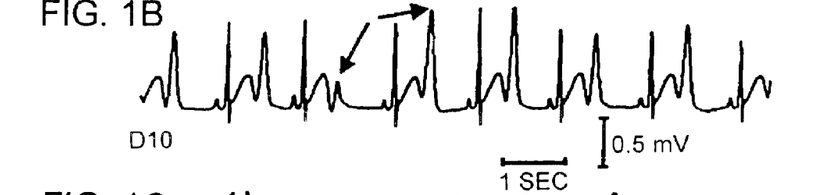
Figure 1C:
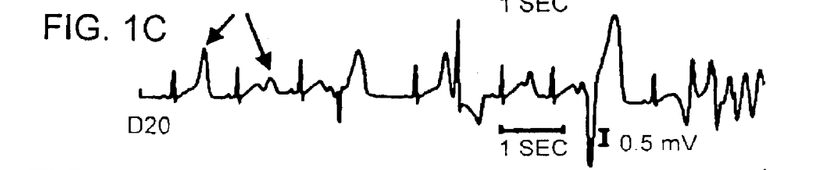
Figure 1D:
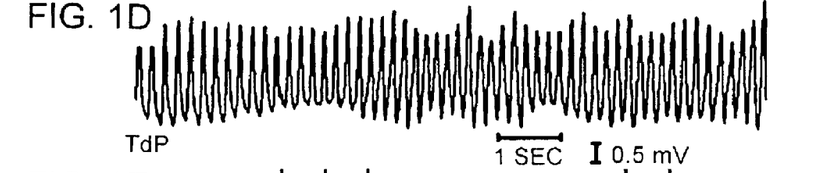
Figure 1E:
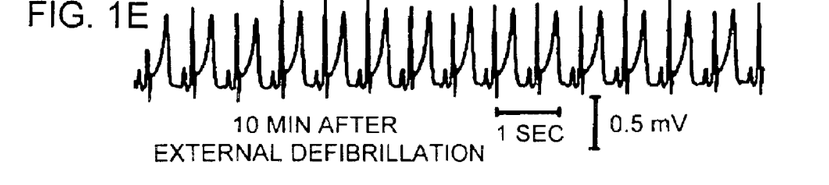
Figure 2A:
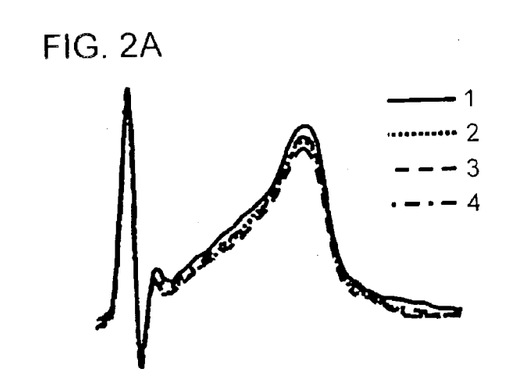
FIG. 2 shows an analysis of the T wave lability observed in the same subject shown in FIG. 1.
Figure 2B:
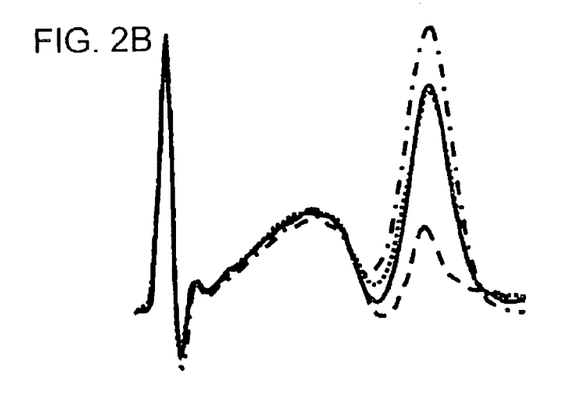
Figure 2C:
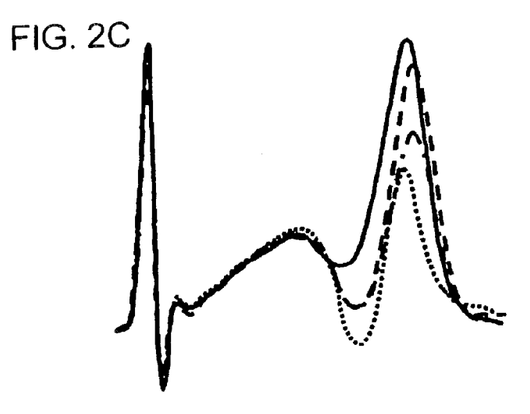
Figure 2D:
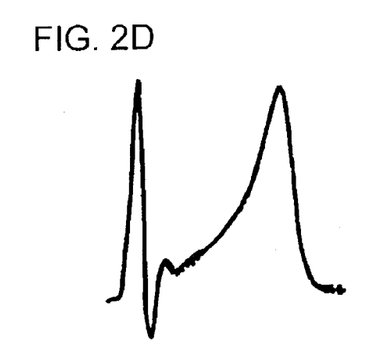
Figure 3A:
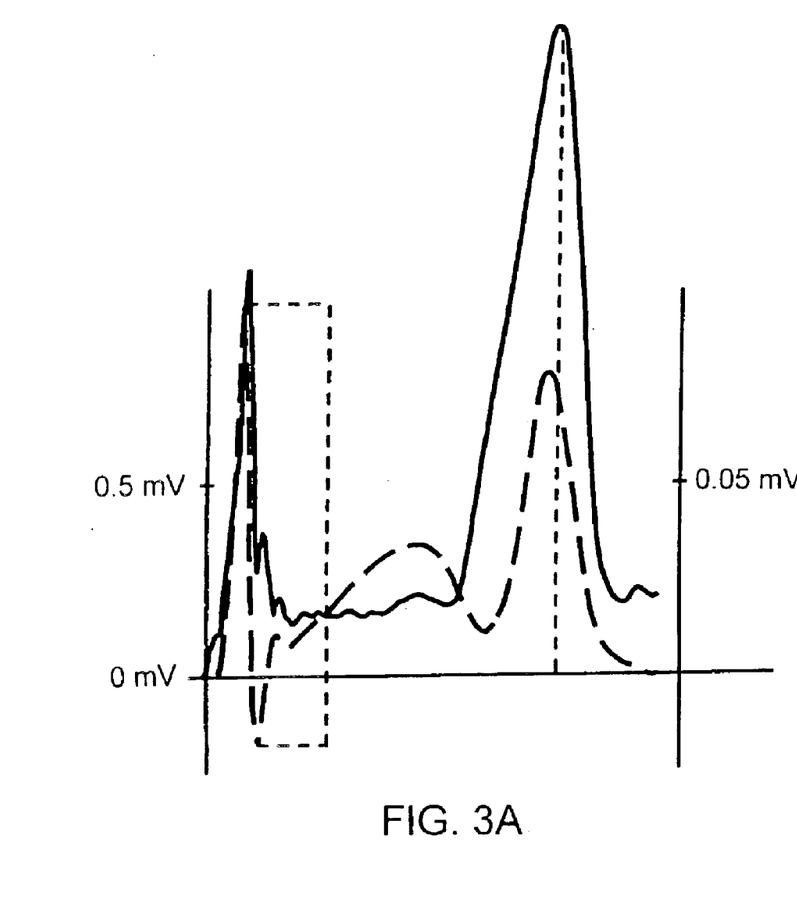
FIG. 3 shows the generation of a T wave lability index (TWLI).
Figure 3B:
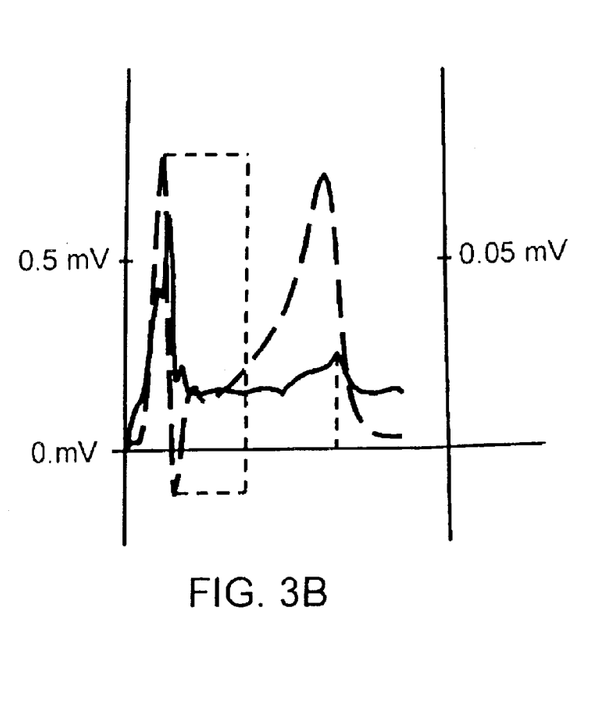

FIG. 3A shows the quantification of T wave lability during dobutamine infusion at 10 $\mu$g/kg/min for the same subject shown in FIGS. 1 and 2. The dotted-line curve shows signal averaged QRST complexes. The solid-line curve plots the root-mean-square differences for each isochronic point (right axis). The vertical dotted line indicates the position having the highest variability of repolarization. The dotted rectangle indicates the absolute magnitude of the QRS complex measured in mVs (left axis). The time interval between the absolute magnitude of the QRS complex and the position of greatest variability of repolarization was 840 msec. The highest variability of repolarization is normalized to the span of the QRS complex to calculate TWLI. For this subject, TWLI=0.148, indicating that the beat-to-beat T wave variability was nearly 15% of the magnitude of the total QRS voltage (T waves are typically about 3% of the magnitude of the total QRS voltage). FIG. 3B shows the corresponding data 10 min following defibrillation. The maximal T wave variability (vertical dotted line) was reduced strikingly (TWLI=0.026).

Figure 4A:
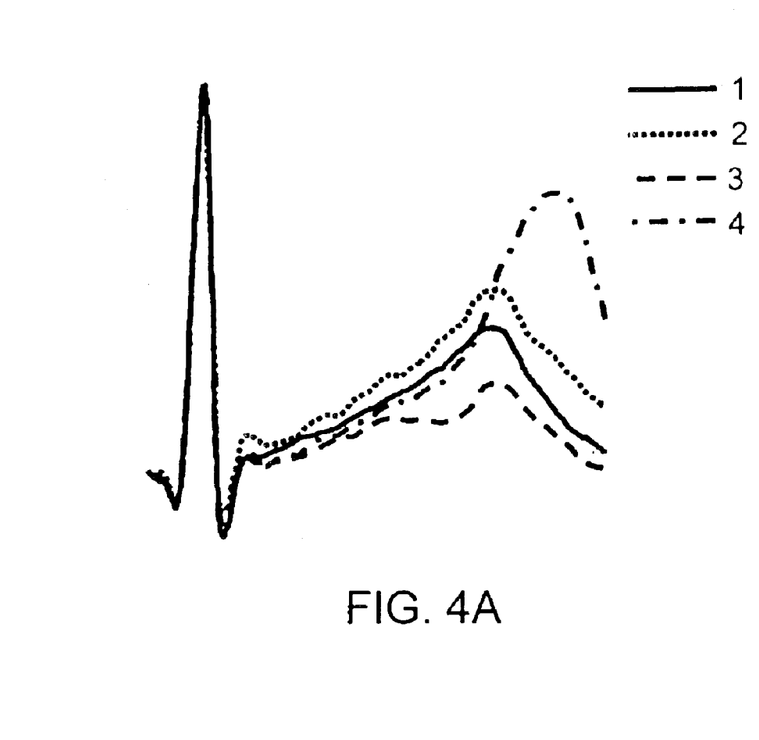
FIG. 4 shows T wave lability in LQT2 and LQT3 subjects.
Figure 4B:
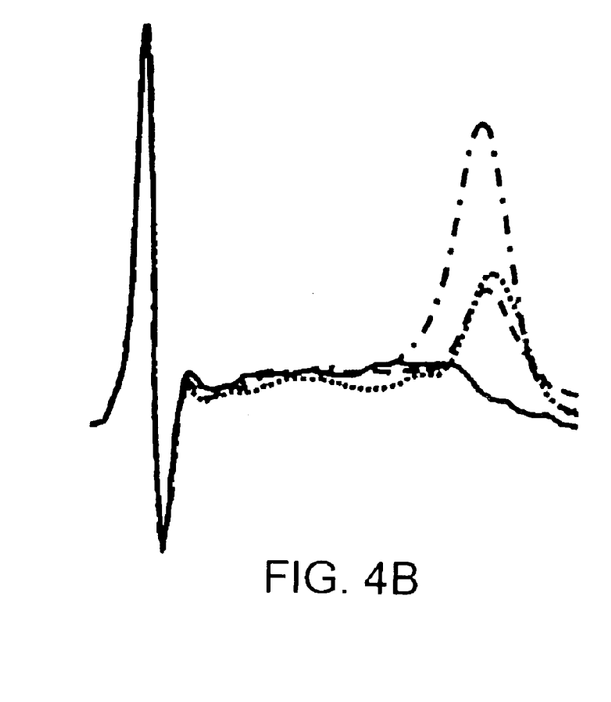

T wave lability also was detected in certain LQT2 and LQT3 patients. FIG. 4A depicts 4 consecutive beats following administration of phenylephrine in a 19 year-old female who presented with an OHCA at age 16 (during a phone conversation) and has a defect in HERG (LQT2, 3080delG stop @ 1056). Her maximum TWLI (0.145) occurred with phenylephrine and, in fact, decreased during dobutamine infusion. FIG. 4B depicts a 14 year-old male with LQT3 (E1784K-SCN5A) exhibited significant T wave lability (TWLI=0.154) at rest. His 12 year-old sister had an increased TWLI seen during phenylephrine-induced bradycardia which decreased during dobutamine infusion.

Figure 5:
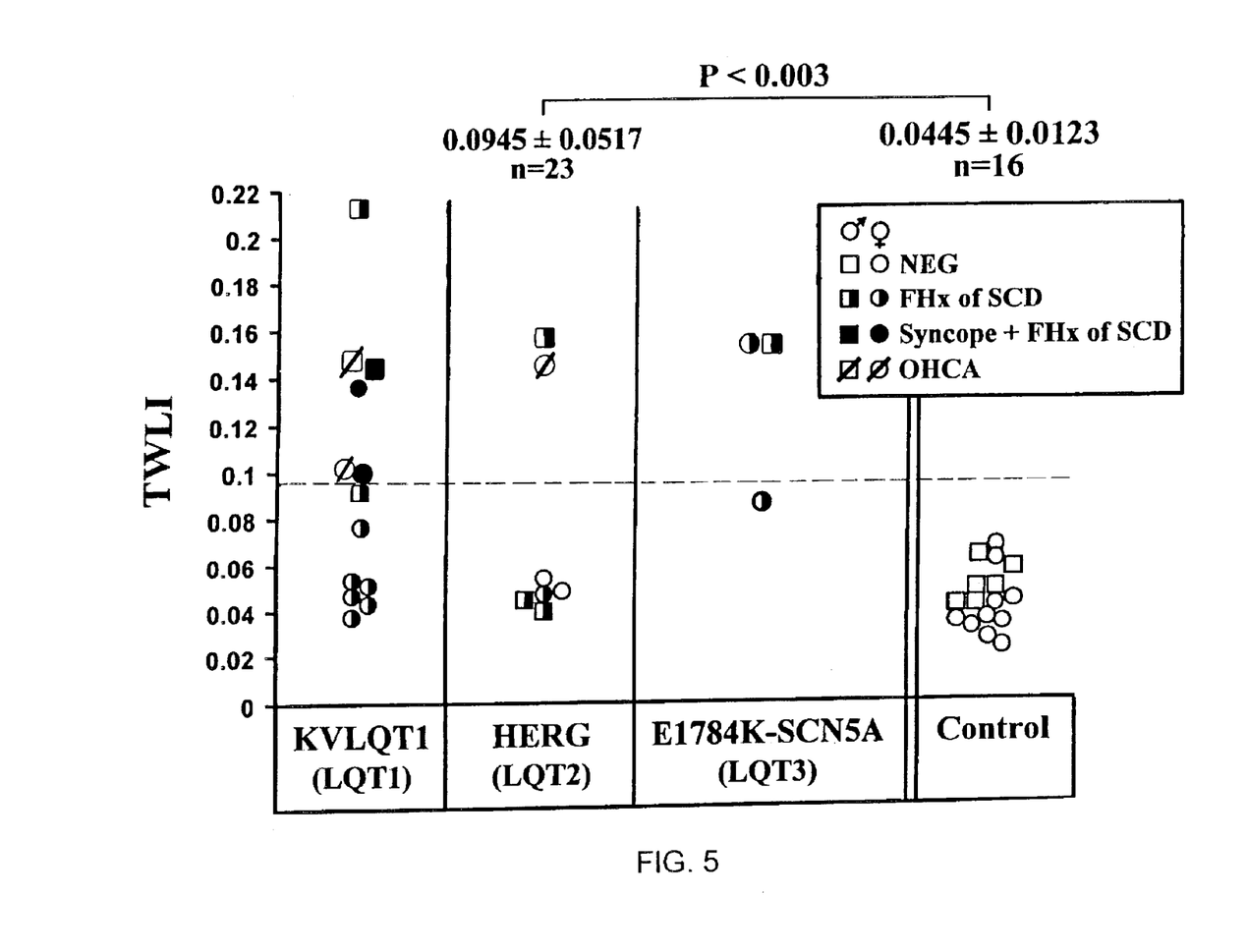
FIG. 5 shows a summary of T wave lability indices (TWLI) in LQTS and control subjects.

The TWLI was significantly higher in LQTS subjects (0.0945±0.0517) than in control subjects (0.0445±0.0123; p<0.003, FIG. 5). Subjects are distinguished on the x-axis by LQTS genotype or by control. Gender of each subject is indicated (squares, males; circles, females). Open symbols denote a negative personal and family history. Partially filled symbols indicate a family history of more than one sudden unexplained death. Filled symbols indicate a personal history of syncope plus a positive family history of sudden death. Symbols with a slash identify those subjects who have experienced an OHCA. Marked T wave lability (TWLI $\geq 0.095$) was present in 10 out of 23 LQTS patients, but was not observed in any control subjects (p<0.003). There was no correlation between TWLI and baseline QTc (r=−0.03, p=−0.91, FIG. 4).

EXAMPLE 9

Risk Stratification Using TWLI

T wave lability (TWLI$\geq$0.095) was associated with the identification of high-risk individuals (p<0.003, FIG. 5). Six out of 23 LQTS patients were deemed high clinical risk by virtue of having either a history of OHCA (3) or a history of syncope with a family history of at least one sudden unexplained death (3). All 6 of these individuals had TWLI$\geq$0.095 at some stage of the study (sensitivity=100% with 95% confidence interval of 54.1% to 100%). In contrast, only 1 of these 6 individuals deemed high clinical risk had a "malignant" QTc (QTc >550 msec). Profound QT prolongation was recorded in a 21-year-old female with LQT1 (V133I-KVLQT1) who presented with OHCA at age 18. Her baseline QTc was 638 msec. She had a TWLI of 0.102 during infusion of 20 $\mu$g/kg/min of dobutamine. Thus, in this study, profound QT prolongation on resting ECG had a sensitivity of 16% (1 out of 6, with a confidence interval of 0.4%–64.1%). All 13 individuals with a TWLI<0.095 were either asymptomatic with no family history of sudden death (2) or solely had a family history of sudden unexplained death (11) as a risk factor.

Curiously, the highest TWLI index (0.213) was recorded during administration of 10 $\mu$g/kg/min dobutamine in a 13-year-old male with LQT1. This individual was entirely asymptomatic and had a screening QTc of 455 msec. His 17-year old brother was found dead in bed 8 mo prior to entering this study. In contrast, this individual's mother had a TWLI=0.043. The next highest TWLI (0.157) recorded and the highest in HERG-based LQT2 was found in a 28-year-old asymptomatic male (N633S-HERG) who has had 7 relatives, including his mother, die prior to the age of 30. Given the family histories and the observation of marked T wave lability, both the 13- and 28-year-old male subjects have received an implantable cardiac defibrillator (ICD) as primary prevention.

A mother and daughter with LQT2 had negative personal and family histories. Their TWLI (0.048 and 0.054, respectively) were indistinguishable from normal subjects, indicating low clinical risk. Fifteen patients with LQTS were asymptomatic, but had a family history of at least one sudden unexplained death. In this case, 8 of the 15 subjects had a normal TWLI.

Finally, T wave lability was investigated in a single LQT3 family. This family was genotyped for an E1784K-SCN5A defect. The mother (age 39), son (age 14), and daughter (age 12) have never had an LQTS-related event. Their maternal grandmother, however, died in her early 50's suddenly and without explanation. In all three LQT3 subjects, the T wave lability index exceeded that of the reference value (i.e., the average T wave lability index for multiple control individuals). In contrast to LQT1 and LQT2, the maximal lability in the LQT3 subjects occurred either at rest or during infusion of phenylephrine.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of assessing the risk of an individual for sudden death due to cardiovascular pathology, the method comprising:
    obtaining T wave signals representative of electrical activity of the heart of said individual;
    detecting the presence of non-alternating fluctuations in T wave morphology for isochronic points between consecutive T waves in said signals; and
    determining a T wave lability index from said non-alternating fluctuations in T wave morphology,
    wherein a T wave lability index that is significantly different than a reference value is indicative of an increased risk of said individual for sudden death due to a cardiovascular disease.

2. The method of claim 1, further comprising administering a chemical stressor to said individual.

3. The method of claim 1, wherein said cardiovascular pathology is selected from the group consisting of long QT syndrome, hypertrophic cardiomyopathy, dilated cardiomyopathy, coronary artery disease, myocardial ischemia, idiopathic ventricular fibrillation and Brugada syndrome.

4. The method of claim 1, wherein said individual presents with QT prolongation, QT variability, ectopy, TWA, OHCA, syncope, angina, late potentials, QT dispersion, wide complex tachycardia, unexplained seizures and unexplained near drownings.

5. A method, the method comprising: identifying non-alternating fluctuations in T wave morphology for isochronic points between consecutive T waves in signals representative of electrical activity of the heart of an individual; and calculating a T wave lability index as a function of said non-alternating fluctuations in T wave morphology.

6. A computer-readable storage medium having instructions stored thereon for causing a programmable processor to:
    identify non-alternating fluctuations in T wave morphology for isochronic points between consecutive T waves in T wave signals representative of electrical activity of the heart of an individual; and
    determine a T wave lability index as a function of said non-alternating fluctuations in T wave morphology.

7. The computer-readable storage medium of claim 6, wherein said determining a T wave lability index as a function of said non-alternating fluctuations in T wave morphology comprises eliminating ectopic beats and sinus beats preceding and following said ectopic beats and calculating the maximal value of root-mean-square differences for isochronic points of a repolarization interval between pairs of consecutive T waves.

8. The computer-readable storage medium of claim 7, wherein said ectopic beats comprise a ventricular premature contraction or an atrial premature contraction.

9. The computer-readable storage medium of claim 7, wherein said determining a T wave lability index as a function of said non-alternating fluctuations in T wave morphology further comprises filtering said signal prior to said calculating.

10. The computer-readable storage medium of claim 7, wherein said determining a T wave lability index as a function of said non-alternating fluctuations in T wave morphology further comprises removing baseline fluctuation from said signal prior to said calculating.

11. The computer-readable storage medium of claim 7, wherein said determining a T wave lability index as a function of said non-alternating fluctuations in T wave morphology further comprises normalizing said maximal value of root-mean-square differences to the absolute magnitude of the signal-averaged QRS complex after said calculating.

* * * * *